United States Patent
Herman et al.

(10) Patent No.: US 9,522,380 B2
(45) Date of Patent: Dec. 20, 2016

(54) CONTROL APPARATUS FOR DISPENSING SMALL PRECISE AMOUNTS OF LIQUID REAGENTS

(71) Applicant: CEM Corporation, Matthews, NC (US)

(72) Inventors: David L. Herman, Charlotte, NC (US); Joseph J. Lambert, Charlotte, NC (US)

(73) Assignee: CEM Corporation, Matthews, NC (US)

( * ) Notice: Subject to any disclaimer, the term of this patent is extended or adjusted under 35 U.S.C. 154(b) by 681 days.

(21) Appl. No.: 13/922,628

(22) Filed: Jun. 20, 2013

(65) Prior Publication Data

US 2014/0374238 A1    Dec. 25, 2014

(51) Int. Cl.
*B01J 19/12*    (2006.01)
*C07K 1/04*    (2006.01)
(Continued)

(52) U.S. Cl.
CPC .............. *B01J 19/126* (2013.01); *B01J 4/008* (2013.01); *B01J 4/02* (2013.01); *B01J 19/0046* (2013.01);
(Continued)

(58) Field of Classification Search
CPC ....... B01J 19/126; B01J 19/0046; B01J 4/008; B01J 4/02; B01J 2219/00164; B01J 2219/1239; B01J 2219/126; B01J 2219/1218; C07K 1/045; G05D 7/0623; G05D 7/0647; F04F 5/24; G01F 11/28; G01F 1/34; Y10T 137/0379; H05B 6/806; H05B 6/6408
See application file for complete search history.

(56) References Cited

U.S. PATENT DOCUMENTS 6,213,354 B1    4/2001 Kay
6,258,329 B1 *  7/2001 Mutterer, Jr. .......... B01J 19/126
                                                        204/157.15
(Continued)

FOREIGN PATENT DOCUMENTS

CN    101598586 A    12/2009
EP    1 533 025 A2    5/2005
(Continued)

OTHER PUBLICATIONS

Extended European Search Report of foreign counterpart European Patent Application No. 14173135.6 mailed Mar. 23, 2015, 3 pgs.
(Continued)

*Primary Examiner* — Xiuyu Tai
(74) *Attorney, Agent, or Firm* — Parsons Summa

(57) ABSTRACT

A precision volumetric liquid dispensing instrument is disclosed that includes two pressure sensors and a fluid passageway with a defined volume portion in communication with the two sensors for receiving and distributing liquid in relatively small volumes. One of the pressure sensors is positioned to measure pressure at one portion of the defined volume portion of the fluid passageway and the other of the gas pressure sensors is positioned to measure gas pressure at a different portion of the defined volume portion of the passageway. At least one valve is in communication with the passageway for moving fluids into or out of the defined volume portion of the fluid passageway, and a processor carries out a step selected from the group consisting of (i) calculating the volume of the liquid based upon the measured pressure and (ii) metering a liquid into the defined volume portion of the fluid passageway until the measured pressure indicates that a desired volume of fluid is in the fluid passageway.

13 Claims, 4 Drawing Sheets

(51) Int. Cl.
    *G05D 7/06*     (2006.01)
    *B01J 19/00*     (2006.01)
    *G01F 11/28*     (2006.01)
    *F04F 5/24*     (2006.01)
    *B01J 4/00*     (2006.01)
    *B01J 4/02*     (2006.01)

(52) U.S. Cl.
    CPC ............... *C07K 1/045* (2013.01); *F04F 5/24* (2013.01); *G01F 11/28* (2013.01); *G05D 7/0623* (2013.01); *G05D 7/0647* (2013.01); *Y10T 137/0379* (2015.04)

(56) References Cited

U.S. PATENT DOCUMENTS

| | | |
|---|---|---|
| 6,288,379 B1 | 9/2001 | Greene et al. |
| 6,744,024 B1 | 6/2004 | Hayes et al. |
| 7,393,920 B2 | 7/2008 | Collins et al. |
| 7,550,560 B2 | 6/2009 | Collins et al. |
| 7,563,865 B2 | 7/2009 | Collins et al. |
| 7,582,728 B2 | 9/2009 | Collins et al. |
| 7,612,165 B2 | 11/2009 | Gjerde |
| 7,902,488 B2 | 3/2011 | Collins et al. |
| 7,939,628 B2 | 5/2011 | Collins et al. |
| 8,058,393 B2 | 11/2011 | Collins et al. |
| 8,153,761 B2 | 4/2012 | Collins et al. |
| 2004/0232162 A1 | 11/2004 | Zimmermann et al. |
| 2005/0045626 A1 | 3/2005 | Collins et al. |
| 2006/0127238 A1 | 6/2006 | Mosier et al. |
| 2011/0286908 A1* | 11/2011 | Matsuuchi ............ A61K 33/00 423/400 |
| 2013/0104668 A1 | 5/2013 | Hanko et al. |

FOREIGN PATENT DOCUMENTS

| | | |
|---|---|---|
| EP | 1 512 975 A2 | 9/2005 |
| JP | 0626906 | 2/1996 |
| JP | H08334394 | 12/1996 |
| JP | 2001526394 | 12/2001 |
| WO | 95/01839 A1 | 1/1995 |
| WO | 01/52991 A1 | 7/2001 |
| WO | 2009035981 A1 | 3/2009 |
| WO | 2011/139234 A1 | 11/2011 |
| WO | 2012064809 A1 | 5/2012 |

OTHER PUBLICATIONS

Partial Search Report of foreign counterpart European Patent Application No. 14173135.6 mailed Dec. 4, 2014, 5 pgs.

* cited by examiner

CONTROL APPARATUS FOR DISPENSING SMALL PRECISE AMOUNTS OF LIQUID REAGENTS

BACKGROUND

The present invention relates to the synthesis of sophisticated compounds or compositions in relatively small amounts (e.g., grams rather than kilograms). The invention is particularly applicable for reactions carried out using complex manipulations (e.g., combinatorial chemistry) or to synthesize complex compositions such as peptides using solid phase peptide synthesis (SPPS).

A number of such processes have been successfully automated and in turn, automation has created a need to dispense and transfer small quantities of liquids accurately and precisely to (among other reasons) obtain a desired reaction, or to minimize the amounts of expensive materials used (avoid waste).

Additionally, depending upon the reaction scheme or desired product, the liquids may have different viscosities or other physical properties that make accurate dispensing of small volumes somewhat difficult. Because of such factors, an automated system should be able to handle a range of viscosities and other liquid properties in order to be most useful over a wide range of substances.

In some circumstances, the difficulty of dispensing small volumes relates to the relatively small openings, tubing or other passageways through which the liquid must pass. These can be susceptible to clogging and other problems.

In some cases, such as solid phase peptide synthesis, a number of reactions are carried out successively using different compositions (e.g., amino acids) that are added in a particular order. For the purpose of adding desired acids to a peptide chain, clogging or even simple residue of a previous acid will tend to cause an increase in the amount of undesired peptide relative to the desired peptide.

In a number of conventional instruments, small dispensed volumes are transferred using devices such as syringe pumps to displace a known volume of liquid into (for example) tubing which carries the liquid to its intended destination. Such techniques are based on the assumption that the volume displaced by the pump will accurately reach the intended location. In an expected manner, however, as required or desired volumes become smaller, relative error increases and in some cases can become significant.

In other applications, precise dispensing of small volumes is carried out using a variety of positive displacement fluid pumps which meter compositions to a desired destination. Nevertheless, such positive displacement pumps tend to be complex and expensive and require considerable maintenance.

Therefore, it remains a continuing goal to obtain accurate automated small volume dispensing systems that can handle liquids within a reasonable range of parameters and accurately dispense those liquids to desired locations.

SUMMARY

In one aspect, the invention is a precision volumetric liquid dispensing instrument that includes two pressure sensors and a fluid passageway with a defined volume portion positioned between the two sensors for receiving and distributing liquid in relatively small volumes. One of the pressure sensors is positioned to measure pressure at one end of the defined volume portion of the fluid passageway and the other of the pressure sensors is positioned to measure pressure at the opposite end of the defined volume portion of said the passageway. At least one valve is in communication with the passageway for moving fluids into or out of the defined volume portion of the fluid passageway, and a processor carries out a step selected from the group consisting of (i) calculating the volume of the liquid between the pressure sensors based upon the measured pressure and (ii) metering a liquid into the defined volume portion of the fluid passageway until the measured pressure indicates that a desired volume of fluid is in the fluid passageway.

In another aspect, the invention is an instrument for solid phase peptide synthesis (SPPS) that includes a microwave cavity and a microwave source for generating microwave radiation and propagating the radiation into the cavity. At least one reaction vessel is in the cavity for containing reagents and carrying out a chemical or physical step on the reagents when the microwave source supplies microwave energy to the cavity. A source reservoir carries source reagents and at least one fluid passageway is between the source reservoir and the reaction vessel for transferring fluids to the reaction vessel. Two pressure sensors are in fluid communication with the fluid passageway and are spaced apart from each other by a defined volume portion of the passageway for measuring pressure in the passageway when a fluid is in the defined volume portion between the pressure sensors. A processor calculates the volume of fluid in the defined volume portion based upon the pressure of the gas between each pressure sensor and the fluid.

In another aspect the invention is a method for transferring precise small volumes of liquids that is particularly useful for solid phase peptide synthesis (SPPS). In this aspect the method includes the steps of transferring a liquid to a defined volume portion of a fluid passageway, maintaining a gas on either side of the liquid in the defined volume portion of the passageway to thereby establish two discrete gas portions with the liquid in the defined volume portion of the passageway between the gas portions, measuring the pressure of at least one of the gas portions, and calculating the volume of transferred liquid in the defined volume portion of the fluid passageway based upon the measured pressure of the gas portion.

In another aspect the invention is a method for transferring precise small volumes of liquids that is particularly useful for solid phase peptide synthesis (SPPS), that includes the steps of measuring the pressure in a defined volume portion of a fluid passageway between two pressure sensors, and adding a liquid to the defined volume portion of the fluid passageway until the measured pressure indicates that a predetermined volume of liquid has been transferred into the passageway between the pressure sensors.

In yet another aspect the invention is a method of metering precise volumes of liquids, concurrently or in succession. In this aspect, the method includes the steps of adding a first liquid from a source of the first liquid to a staging area that contains at least some gas until the change of pressure in the gas indicates that a desired volume of the first liquid is in the staging area, segregating the first source from the staging area, adding a second liquid to the same staging area as the first liquid and separated from the first liquid by a gas portion until the change of pressure of the gas in the staging area indicates that a desired volume of the second liquid is in the staging area, segregating the second source from the staging area, and thereafter adding the first and second liquids to a reaction vessel in a single step.

The foregoing and other objects and advantages of the invention and the manner in which the same are accom-

DETAILED DESCRIPTION

The invention is a control apparatus for dispensing small and precise amounts of liquid reagents. The invention is particularly useful in microwave assisted chemistry, including microwave assisted solid phase peptide synthesis (SPPS).

Figure 1:
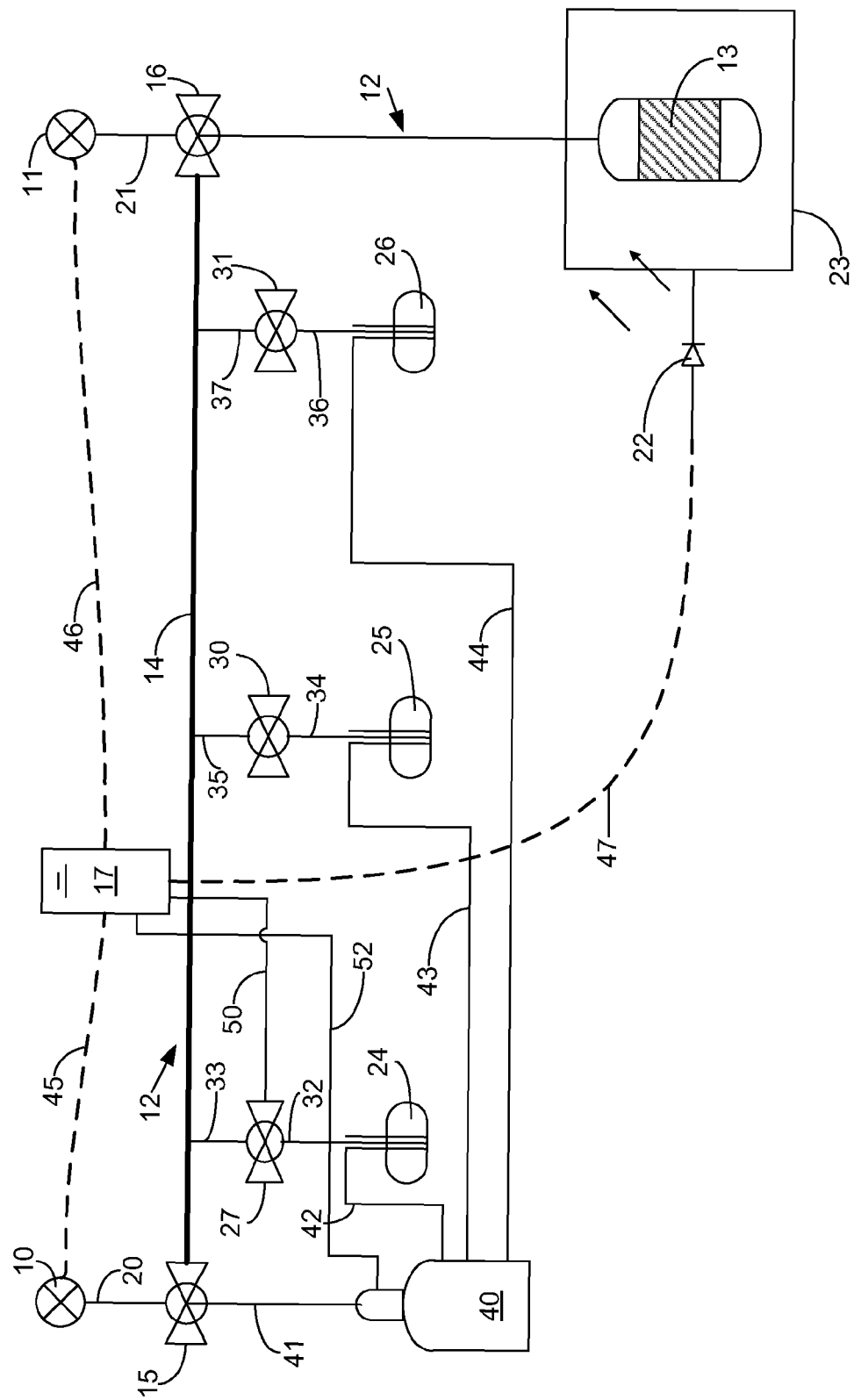
FIGS. 1-4 are schematic diagrams of the instrument and method of the invention.

FIG. 1 is a schematic diagram of the invention. Because the fundamental parts are well understood and can be selected from a variety of choices without undue experimentation, the schematic view is a clear and helpful method of presenting the invention.

The invention includes two pressure sensors 10 and 11. A fluid passageway 12, which in an SPPS instrument is often a portion of small diameter tubing, travels between the two sensors 10 and 11 and eventually reaches a reaction vessel 13. A portion of the passageway 12 has a specifically defined volume which in FIG. 1 is labeled at 14 between the two valves 15 and 16 that are in communication with the liquid passageway 12. It will be understood that FIG. 1 illustrates an exemplary positioning of the sensors 10, 11 and the defined volume portion 14 rather than a single limiting set of positions.

One of the pressure sensors 10, 11 is positioned to measure gas pressure at one portion (at one end in the illustrated embodiment) of the defined volume portion 14 of the fluid passageway 12, and the other gas pressure sensor is positioned to measure gas pressure at another portion (here, the opposite end) of the defined volume portion 14 of the fluid passageway 12. One or more of the valves 27, 30, 31 are used to move fluid into or out of the defined volume portion 14 of the fluid passageway 12.

In this manner, the defined volume portion 14 will initially be empty of liquid and then will contain some liquid and some gas. The gas can be an atmospheric ambient or another gas supplied intentionally, and usually being inert with respect to the reagents, products, and the material forming the passageway. Liquid added to the defined volume portion 14 will, of course, displace the gas. In the invention, however, the displaced gas is captured in the defined volume portion 14 with the result that the added liquid forces the gas volume to decrease. In accordance with well understood principles (most typical of which is the ideal gas law) the change in gas volume is accurately reflected in the change of gas pressure. In further accordance with fluid mechanics, the pressure of the gas-liquid system is the same as the gas pressure alone. As a result, pressure measurements can be taken of gas or liquid to obtain the relevant data.

A processor 17 carries out a step selected from the group consisting of (i) calculating the volume of the liquid based upon the measured pressure and (ii) metering a liquid into the defined volume portion 14 of the fluid passageway 12 until the measured pressure indicates that the desired volume of fluid is in the fluid passageway 12. In the illustrated embodiment the pressure is measured by the pressure sensors 10, 11.

In FIG. 1, the gas pressure sensors 10, 11 are shown in communication with the respective valves 15, 16 through two pressure lines 20, 21. In other embodiments, the gas pressure sensors 10, 11 can be incorporated as part of the valves 15, 16 thus eliminating the need for the pressure lines 20, 21. The sensors can also be positioned more directly in fluid communication (gas or liquid) with the defined volume portion 14. These adjustments can be made by persons of ordinary skill in this art without undue experimentation.

As set forth in the background, the invention is particularly useful for solid phase peptide synthesis (SPPS) and in particular for microwave assisted SPPS as described in commonly assigned U.S. Pat. No. 7,393,920. The contents of U.S. Pat. No. 7,393,920 and it commonly-assigned siblings (U.S. Pat. Nos. 7,939,628; 7,550,560; 7,563,865; 7,902,488; 7,582,728; 8,153,761; and 8,058,393) are incorporated entirely herein by reference.

Accordingly, FIG. 1 further schematically illustrates a microwave source 22. Typical sources are selected from the group consisting of magnetrons, klystrons, and IMPATT diodes. These can be selected by persons of ordinary skill in the art without undue experimentation. In most cases, a magnetron provides a robust, reliable and cost effective source, particularly for the regulated frequencies at which laboratory equipment operates, and of which 2450 MHz is common.

The source 22 propagates the microwaves into a cavity schematically illustrated as the rectangle 23. It will be understood that in this context, the term "cavity" describes an enclosure that will contain and reflect the microwaves. For robust reactions (such as acid digestion or drying), the cavity is generally defined by six metal sides that define the interior as a rectangular solid. For more sensitive organic reactions including SPPS, the cavity is typically more sophisticated, and usually a single mode cavity of the type described in the aforementioned patents or alternatively in commonly assigned U.S. Pat. Nos. 6,288,379 or 6,744,024 (the contents of which are likewise incorporated entirely herein by reference). In turn, persons of skill in this art recognize that a single mode is generated and supported when the propagated frequency and the size and shape of cavity complement one another.

As illustrated in FIG. 1, the reaction vessel 13 is positioned in the microwave cavity 23 and is in fluid communication with the fluid passageway 12 at a position other than the defined volume portion 14. In FIG. 1, this relationship is illustrated by positioning the reaction vessel 13 downstream of the valve 16.

FIG. 1 also illustrates at least one source reservoir 24, and in exemplary embodiments a plurality of source reservoirs, which in FIG. 1 are indicated at 25 and 26. In the exemplary embodiments and as illustrated in FIG. 1 each of the reservoirs 24, 25, 26 connects to the defined volume portion 14 of the fluid passageway 12 between the pressure sensors 10, 11 and in the illustrated embodiment specifically between the valves 15, 16.

Respective liquid valves 27, 30, and 31 are associated with the source reservoirs 24, 25, 26. The individual source reservoirs 24, 25, 26 each independently communicates with the defined volume portion 14 of the fluid passageway 12 between the gas pressure sensors 10, 11. Respective liquid lines 32, 33 are associated with the source reservoir 24 for this purpose, and similar pairs of lines 34, 35 and 36, 37 are respectively associated with the source reservoirs 25 and 26.

FIG. 1 further illustrates that in exemplary embodiments a gas supply 40 is in communication with the defined volume portion 14 of the fluid passageway 12, for transferring gas from the gas supply 40 into the passageway 12 to push liquid in the passageway to the reaction vessel 13. In the illustrated embodiment, an appropriate gas line 41 connects the gas supply 40 to the defined volume portion 14 through the valve 15.

It will be understood that any appropriate gas can be used for this purpose, provided that the gas is inert with respect to the liquids being transferred and to the mechanical parts of the instrument. In many cases, including SPPS, nitrogen is a cost effective choice. Of course, in reactions in which nitrogen gas would serve as a reactant, another gas is selected. Specific choices, however, are well understood in the chemical arts and need not be repeated here.

In the same manner, the invention can include a gas supply in communication with any one or more of the source reservoirs 24, 25, 26 for pushing liquid from the source reservoir into the fluid passageway 12. The gas supply that is in communication with the reservoirs 24, 25, 26 can be the same or different from the gas supply 40 that is in communication with the defined volume portion 14. In the illustrated embodiment, the same gas supply 40 delivers nitrogen both to the defined volume portion 14 of the passageway 12 and to each of the reservoirs 24, 25, 26. For this purpose, gas lines 42, 43, and 44 respectively connect the gas supply 40 to the source reservoirs 24, 25, and 26.

In another aspect, the invention is a method for transferring precise small amounts of liquids that is particularly useful for solid phase peptide synthesis. The method includes the steps of transferring a liquid to the defined volume portion 14 of the fluid passageway 12. A gas is maintained with the liquid (as illustrated, on either side of the liquid) in the defined volume portion 14 of the passageway to thereby establish at least one (and potentially two) discrete gas portion with the liquid in the defined volume portion 14 of the passageway 12. The pressure in the defined volume portion 14 is measured by one of the sensors 10, 11, and the volume of liquid in the defined volume portion 14 is calculated based upon the measured pressure.

In most cases, the calculation is carried out by the processor 17 which communicates with the pressure sensors 10 and 11 through the signal wires 45 and 46 respectively. The pressure in the defined volume portion 14 relates directly to the volume of the gas (and thus the volume of the liquid) in accordance with well understood relationships such as Boyles law ($P_1V_1=P_2V_2$) or the ideal gas law ($PV=nRT$). If desired or necessary, one of the more sophisticated versions of the gas laws can be used, and other corrections can be incorporated such as accounting for flexibility in plastic parts such as tubing that might expand slightly under pressure.

The processor 17 can also be used to control various aspects of the source 22 or any other appropriate items. This relationship is illustrated by the wire 47 from the processor 17 to the diodes 22. FIG. 1 also shows that in some embodiments, the processor 17 can communicate with the valve 27 through line 50 to control or help control the flow of fluid between the source reservoir 24 and the fluid passageway 12. Similarly, the line 52 connects the processor 17 to the gas supply 40 (e.g., using a regulator) to control or help control the use of the gas to move fluids throughout the relevant portions of the instrument.

It will be understood that similar connections can exist between and among the processor 17 and the other valves and reservoirs. For purposes of clarity, however, these are not specifically illustrated in the figures.

This aspect of the invention provides a time shifting advantage in synthesis as well. In particular, one reaction (or one step) with certain reagents can be carried out in the reaction vessel 13 while the next reagent can be loaded from one of the reservoirs into the defined volume portion of the passageway 12. The method thus includes the step of transferring the liquid from one (or several) of the source reservoirs 24, 25, 26 to the defined volume portion 14 of the fluid passageway 12 and then transferring the liquid to a reaction vessel 13 based upon the measured pressure.

In practice, separate items of liquid can be added, and if reaction in the tube needs to be prevented, the items can be separated in the tube using a gas portion. This permits liquid to be added serially in a timesaving manner.

In the context of SPPS the method comprises transferring a liquid for one (or more) of the SPPS steps. Thus, the method comprises transferring a liquid selected from the group of amino acids, activators, deprotecting agents, solvents and cleaning agents to the reaction vessel 13 which in the SPPS context will typically contain at least one amino acid (and potentially a growing peptide) linked to a solid phase resin.

In the microwave-assisted context, the method further comprise applying microwave radiation to the reaction vessel 13 to carry out one of the SPPS reaction steps which include deprotecting an amino acid, activating an amino acid, washing a resin-linked amino acid with a solvent, and cleaving an amino acid from a solid phase resin.

Because of the predictable behavior of gases under normal conditions (as expressed by Boyle's law and the ideal gas law), the method can also be carried out slightly differently. In another method aspect, the invention comprises measuring the gas pressure in a defined volume portion 14 of the fluid passageway 12 between the two pressure sensors 10, 11 and then adding a liquid to the defined volume portion 14 of the fluid passageway 12 until the measured pressure indicates that a predetermined volume of liquid has been transferred into the passageway between the pressure sensors.

It will be understood that if the size of the defined volume portion 14 is well understood, and if other factors do not come into play, only the pressure in the defined volume portion 14 measured by one of the pressure sensors 10, 11 is necessary to calculate the liquid volume. In a practical instrument context, however, portions of the fluid passageway 12 and of the defined volume portion 14 are almost always necessarily or favorably positioned other than horizontally. In such cases, the weight of the liquid (rather than the volume of the liquid) may compress the gas portion. As a result, the pressure reading will not necessarily accurately reflect the liquid volume. The use of two pressure sensors, however, avoids this problem because the pressure independent of gravity can always be measured and an appropriate volume calculated.

Figure 2:
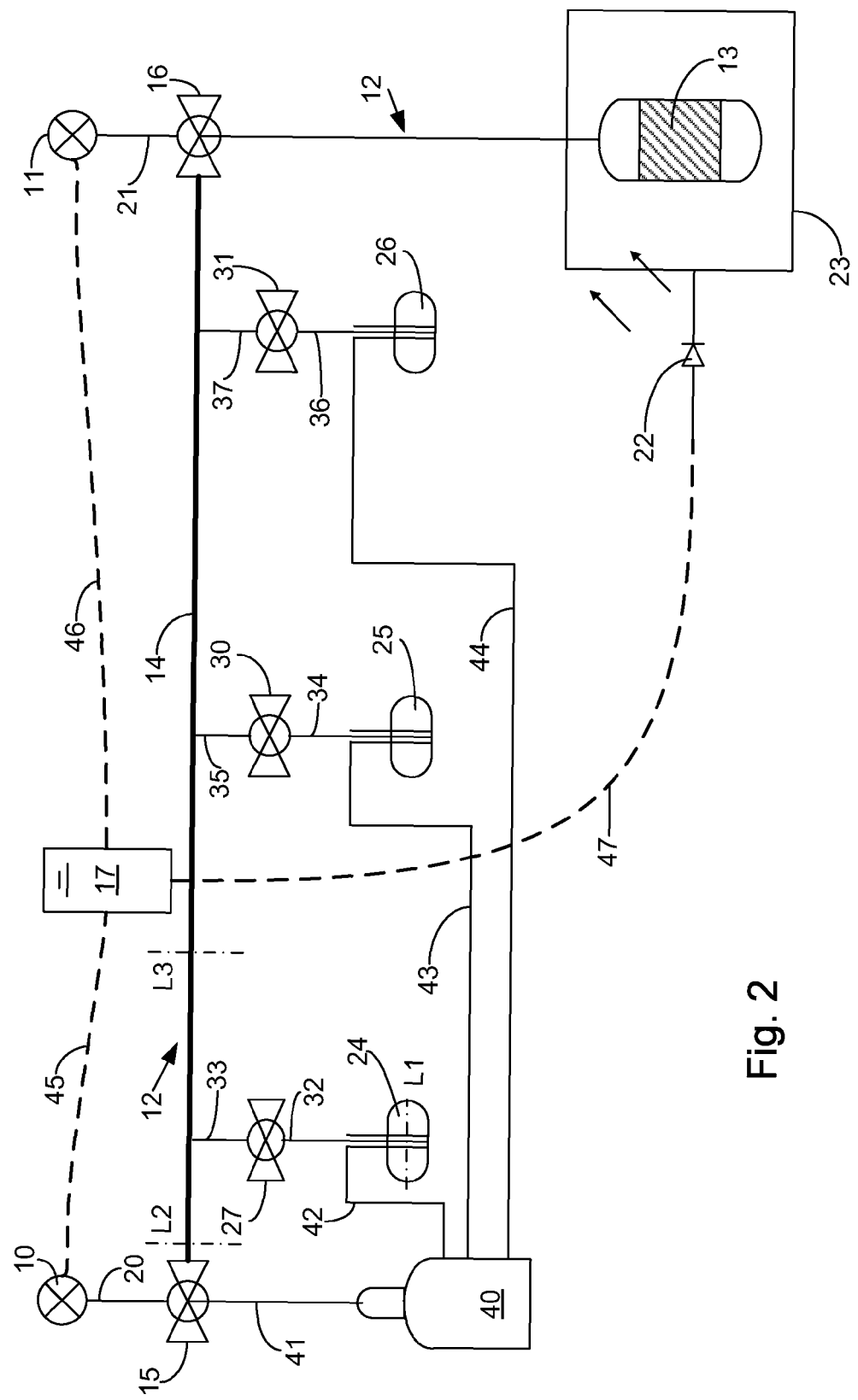
Figure 3:
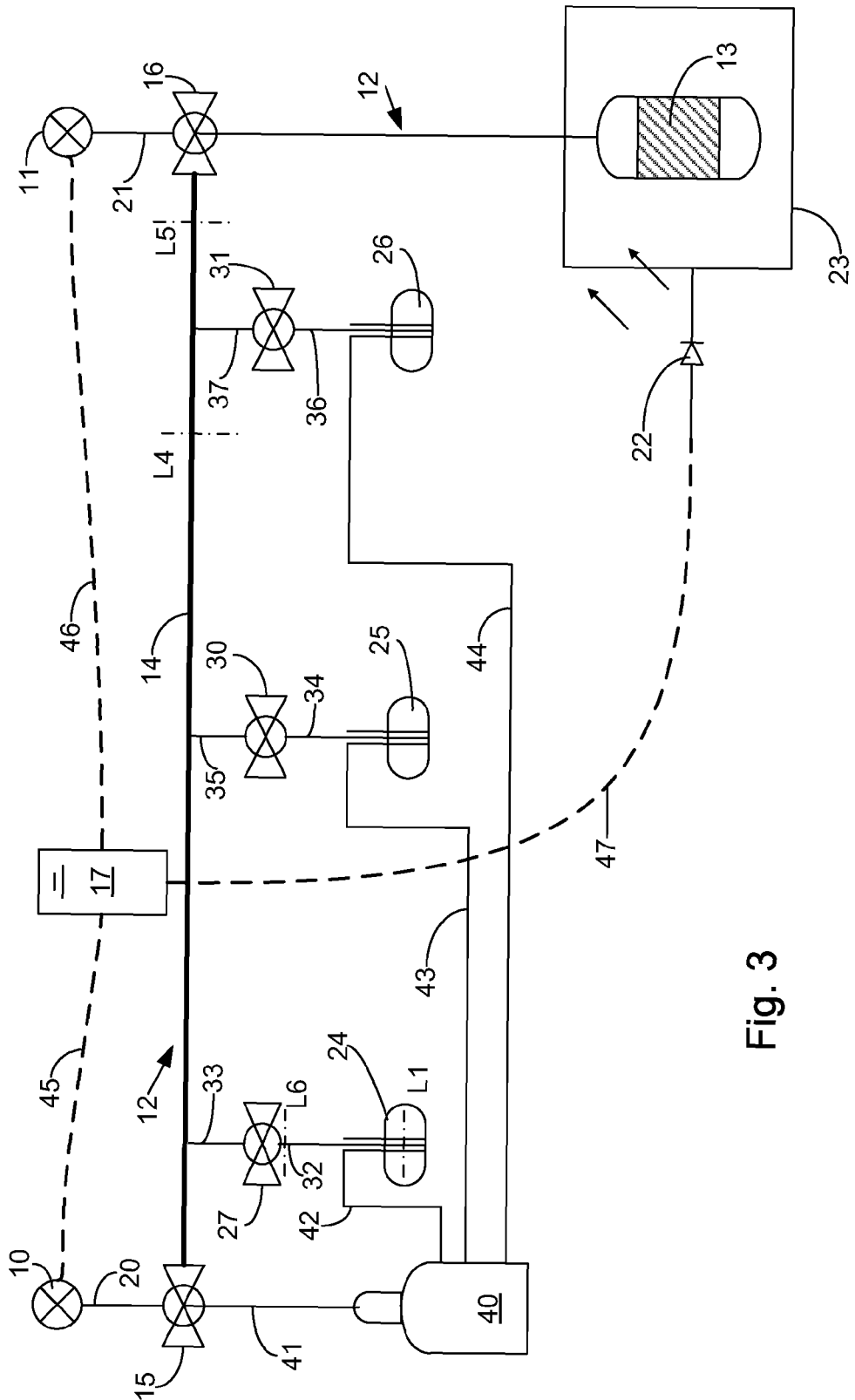

FIGS. 2 and 3 are schematic diagrams essentially identical to FIG. 1, but marking exemplary positions of a fluid to illustrate aspects of the invention. FIG. 2 illustrates a portion of liquid dispensed from the source reservoir 24 and into a portion of the defined volume portion 14. For schematic purposes, the liquid position is identified by the three boundary lines L1, L2, and L3. As previously described, nitrogen gas provided from the source 40 travels through the line 42 and urges liquid in the source reservoir 24 to move into the defined volume portion 14. FIG. 2 further illustrates that appropriate pressure measurements can be taken upon the gas that has been compressed between L2 and the pressure sensor 10 and additionally or alternatively the pressure can be measured between the other edge of the liquid L3 and the other pressure sensor 11.

FIG. 3 illustrates the position of a liquid sample after the valve 27 has been closed and after gas from the source 40 pushes liquid further within the defined volume passage 14 towards the reaction vessel 13. In FIG. 3, the liquid between the source reservoir 24 and the valve 27 is schematically indicated by the lines L1 and L6. The boundaries of the liquid moving towards the reaction vessel 13 are indicated by the lines L4 and L5.

Figure 4:
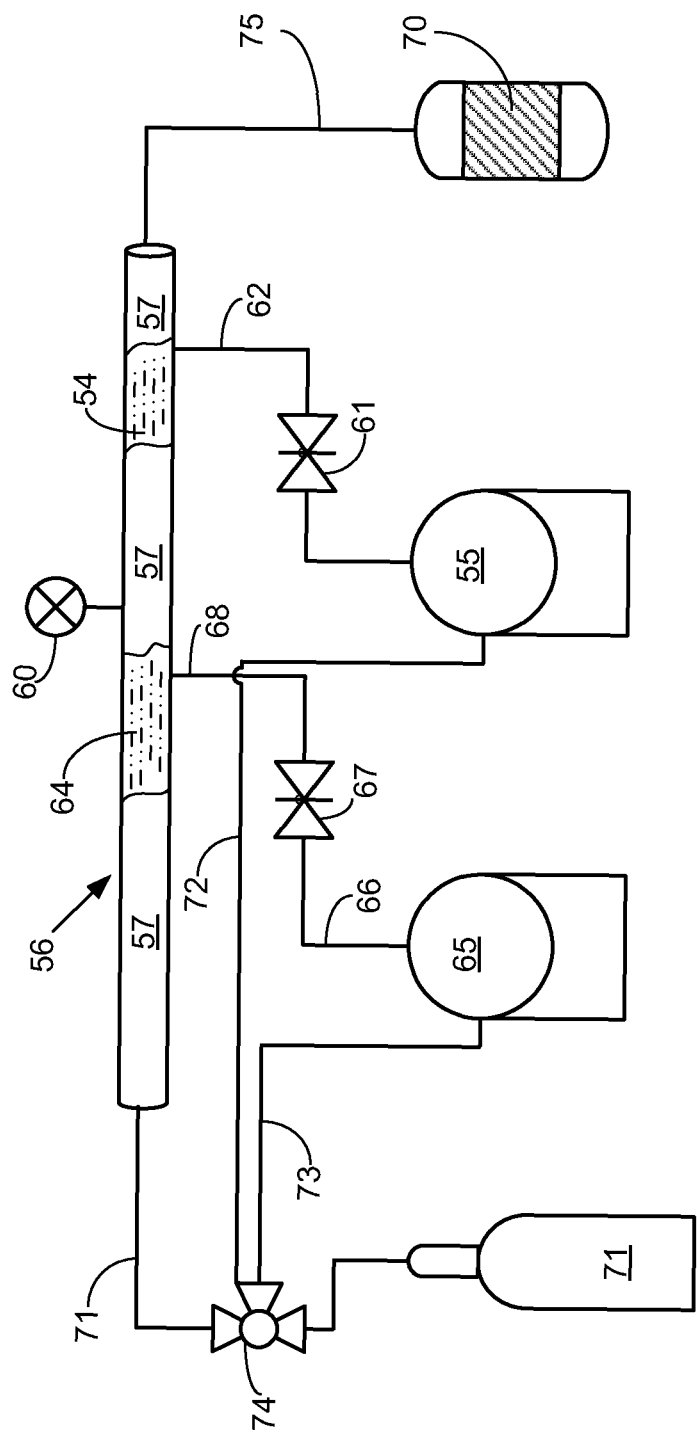

FIG. 4 illustrates another method according to the invention. In this context, the method of metering precise volumes of liquids can be carried out concurrently or in succession. A first liquid 54 is added from a source 55 of the first liquid to a staging area broadly designated at 56. The staging area 56 includes at least some gas, which is present in one or more areas designated at 57. The gas pressure is measured with the gas pressure sensor 60 which in any or all respects can be the same as the gas pressure sensors 10 and 11 in FIGS. 1-3. The first liquid 54 is added to the staging area 56 until the change of pressure in the gas portion 57 as measured by the sensor 60 indicates that the desired volume of the first liquid 54 is in the staging area 56.

The source 55 is then segregated from the staging area 56, and this segregation is typically is carried out by closing a valve 61 in the line 62 through which the first liquid 54 is added to the staging area 56.

In the next step, a second liquid 64 is added to the same staging area 56 as the first liquid 54 and is separated from the first liquid 54 by one of the gas portions 57. The second liquid 64 is added from a second liquid source 65 through a corresponding line 66 and valve 67 until the change in the pressure of the gas 57 in the staging area 56 indicates that the desired volume of the second liquid 64 is in the staging area 56. At this point the staging area is segregated from the source of second liquid 65 again typically using the valve 67.

It will be understood that when the staging area is (for simplicity of explanation) both empty and closed, the gas 57 will exhibit a certain pressure (atmospheric pressure in many cases). As the first liquid 54 is added to the otherwise closed staging area 56, the pressure increases in inverse proportion to the change in the gas volume in the staging area. When the second liquid 64 is added, the pressure increases yet again, and the second increase in pressure is directly proportional to the volume of added second liquid.

As the last step, the first and second liquids 54, 64 can be added to the reaction vessel 70 immediately after one another, and at this point they can mix in the reaction vessel 70 and react there in the intended manner.

FIG. 4 illustrates that a convenient method of moving the fluids is with a gas supply 71 connected to the staging area 56 through the line 71. The gas supply 71 is also connected to the first liquid supply 55 through the line 72 and to the second liquid supply through the line 73. A multiport valve 74 directs the gas as desired to push either the source liquids into the staging area 56 or to push liquids already in the staging area 56 from the staging area to the reaction vessel 70.

FIG. 4 illustrates the staging area as long and cylindrical (relatively speaking) because in many applications, the staging area 56 will be tubing that connects the liquid supplies 55, 65 to the staging area and the staging area to the reaction vessel 70 through the line 75.

The method provides the advantage of having multiple reactants both present and segregated in a staging area, typically a supply line, from which the liquids can be added quickly together to reaction vessel. Because the liquids are nevertheless maintained segregated in the supply line, the method avoids undesired (typically premature) reactions in the supply line.

The method offers a significant time savings in automated systems because otherwise a complete cycle of adding each portion of liquid successively would be required.

It will be understood that additional (third, fourth, etc.) samples of liquid can be added to the staging area behind the first and second liquids in the method, and that the number of liquids that can be added in this manner is limited only by space and the desired or necessary complexity of the fluid handling equipment. In peptide synthesis, because of the sequential and discrete nature of the desired reactions, usually between two and four liquid compositions are added to the staging area 56 for any given reaction step in the SPPS cycle.

In the drawings and specification there has been set forth a preferred embodiment of the invention, and although specific terms have been employed, they are used in a generic and descriptive sense only and not for purposes of limitation, the scope of the invention being defined in the claims.

The invention claimed is:

1. A precision volumetric liquid dispensing instrument comprising:
   two pressure sensors;
   a fluid passageway for receiving and distributing liquid having a defined volume portion positioned in fluid connection with said two sensors;
   one of said pressure sensors being positioned to measure pressure at one portion of said defined volume portion of said fluid passageway and the other of said pressure sensors being positioned to measure gas pressure at a different portion of said defined volume portion of said fluid passageway;
   at least one valve in communication with said passageway for moving fluids into or out of said defined volume portion of said fluid passageway;
   a processor for carrying out a step selected from the group consisting of (i) calculating the volume of a liquid added to said defined volume portion based upon the measured pressure and (ii) metering a liquid into said defined volume portion of said fluid passageway until the measured pressure indicates that a desired volume of fluid is in said fluid passageway;
   a microwave source;
   a microwave cavity in communication with said source; and
   a reaction vessel in said microwave cavity and in fluid communication with said fluid passageway at a position other than said defined volume portion.

2. A precision volumetric liquid dispensing instrument according to claim 1 wherein said defined volume portion is positioned between said two pressure sensors.

3. A precision volumetric liquid dispensing instrument according to claim 1 further comprising a source reservoir that connects to said defined volume fluid passageway at a point between said two gas pressure sensors.

4. A precision volumetric liquid dispensing instrument according to claim 1 further comprising a plurality of source reservoirs, and wherein each said reservoir connects to said defined volume portion of said fluid passageway.

5. An instrument for solid phase peptide synthesis (SPPS) comprising:
   a microwave cavity;
   a microwave source for generating microwave radiation and propagating the radiation into said cavity;
   a source reservoir for reagents;
   at least one reaction vessel in said cavity for containing reagents and carrying out a chemical or physical step on the reagents when said microwave source supplies microwave energy to said cavity;

at least one fluid passageway between said source reservoir and said reaction vessels for transferring fluids to said reaction vessel;

two pressure sensors in fluid communication with said at least one fluid passageway and spaced apart from each other by a defined volume portion of said at least one passageway for measuring pressure in said at least one fluid passageway when a fluid is in said defined volume portion between said pressure sensors; and a processor for calculating the volume of fluid in said defined volume portion based upon the pressure of the gas between each pressure sensor and the fluid.

6. An SPPS instrument according to claim 5 wherein said source reservoir communicates with said defined volume portion of said at least one fluid passageway between said two gas pressure sensors, and said reaction vessel communicates with said fluid passageway at a position other than said defined volume portion.

7. An SPPS instrument according to claim 6 further comprising a liquid valve between said source reservoir and said defined volume portion of said at least one fluid passageway.

8. An SPPS instrument according to claim 5 comprising a plurality of source reservoirs, each of which independently communicates with said defined volume portion of said at least one fluid passageway between said gas pressure sensors.

9. An SPPS instrument according to claim 8 further comprising a liquid valve between each said source reservoir and said defined volume portion of said at least one fluid passageway.

10. An SPPS instrument according to claim 5 further comprising a liquid valve between one of said pressure sensors and said reaction vessel for distributing liquid to said reaction vessel from said defined volume portion of said at least one fluid passageway.

11. An SPPS instrument according to claim 10 further comprising:

a gas supply in communication with said defined volume portion of said at least one fluid passageway; and a gas valve between said gas supply and said defined volume portion of said fluid passageway for transferring gas from said gas supply into said passageway to push liquid in said passageway to said reaction vessel.

12. An SPPS instrument according to claim 5 further comprising a gas supply in communication with said source reservoir for pushing liquid in said source reservoir into said at least one fluid passageway.

13. An SPPS instrument according to claim 5 wherein said at least one fluid passageway is a tube with a defined liquid volume between two gas pressure sensors.

* * * * *